(12) United States Patent
Oh et al.

(10) Patent No.: US 12,708,280 B2
(45) Date of Patent: Aug. 18, 2026

(54) DEVICE AND METHOD FOR PRECISELY MEASURING SKIN MOISTURE

(71) Applicant: INDUSTRY-ACADEMIC COOPERATION FOUNDATION, YONSEI UNIVERSITY, Seoul (KR)

(72) Inventors: Seung Jae Oh, Gwangmyeong-si (KR); In Hee Maeng, Goyang-si (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 291 days.

(21) Appl. No.: 18/571,064

(22) PCT Filed: Jan. 12, 2023

(86) PCT No.: PCT/KR2023/000550
§ 371 (c)(1),
(2) Date: Dec. 15, 2023

(87) PCT Pub. No.: WO2024/117379
PCT Pub. Date: Jun. 6, 2024

(65) Prior Publication Data

US 2025/0098975 A1 Mar. 27, 2025

(30) Foreign Application Priority Data

Nov. 30, 2022 (KR) ........................ 10-2022-0164351
Jan. 12, 2023 (KR) ........................ 10-2023-0004540

(51) Int. Cl.
*A61B 5/0507* (2021.01)
*A61B 5/00* (2006.01)

(52) U.S. Cl.
CPC .......... *A61B 5/0507* (2013.01); *A61B 5/4875* (2013.01); *A61B 5/6843* (2013.01)

(58) Field of Classification Search
CPC .......... A61B 2018/00452; A61B 2018/00458; A61B 2018/00464; A61B 2018/0047;
(Continued)

(56) References Cited

U.S. PATENT DOCUMENTS

2019/0246963 A1* 8/2019 Chung ............... A61B 5/14532
2020/0205895 A1* 7/2020 Butterworth ....... A61B 18/1815

FOREIGN PATENT DOCUMENTS

CN 213606300 U 7/2021
JP 10094522 A 4/1998
(Continued)

OTHER PUBLICATIONS

Lindley-Hatcher, H. et al. "Evaluation of in vivo THz sensing for assessing human skin hydration." J. Phys. Photonics 3 014001 (2021) (Year: 2021).*

*Primary Examiner* — Keith M Raymond
*Assistant Examiner* — Milton Truong
(74) *Attorney, Agent, or Firm* — Dority & Manning, PA

(57) ABSTRACT

The present disclosure relates to a device and method for precisely measuring skin moisture, and more particularly, to a device and method for precisely measuring skin moisture in which measurement of skin moisture is not affected by pressure applied to the device. A device for precisely measuring skin moisture according to one aspect of the present disclosure may include a main body which is open toward a measurement target and has a hollow portion, a contact part slidably mounted on the main body and having a window provided thereon to come in contact with the measurement target, and a connector which includes an elastic member provided to connect the main body and the contact part and be compressed during sliding of the contact part into the main body.

6 Claims, 6 Drawing Sheets

(58) Field of Classification Search
CPC ... A61B 5/0507; A61B 5/4875; A61B 5/6843; A61B 5/00
See application file for complete search history.

(56) References Cited

FOREIGN PATENT DOCUMENTS

| | | | | | |
|---|---|---|---|---|---|
| JP | 2009028275 | A | * | 2/2009 | |
| JP | 2009515663 | A | | 4/2009 | |
| JP | 2017201254 | A | | 11/2017 | |
| KR | 20190060488 | A | | 6/2019 | |
| WO | WO-2005092438 | A1 | * | 10/2005 | ............ A61N 5/067 |

* cited by examiner

[FIG. 1]
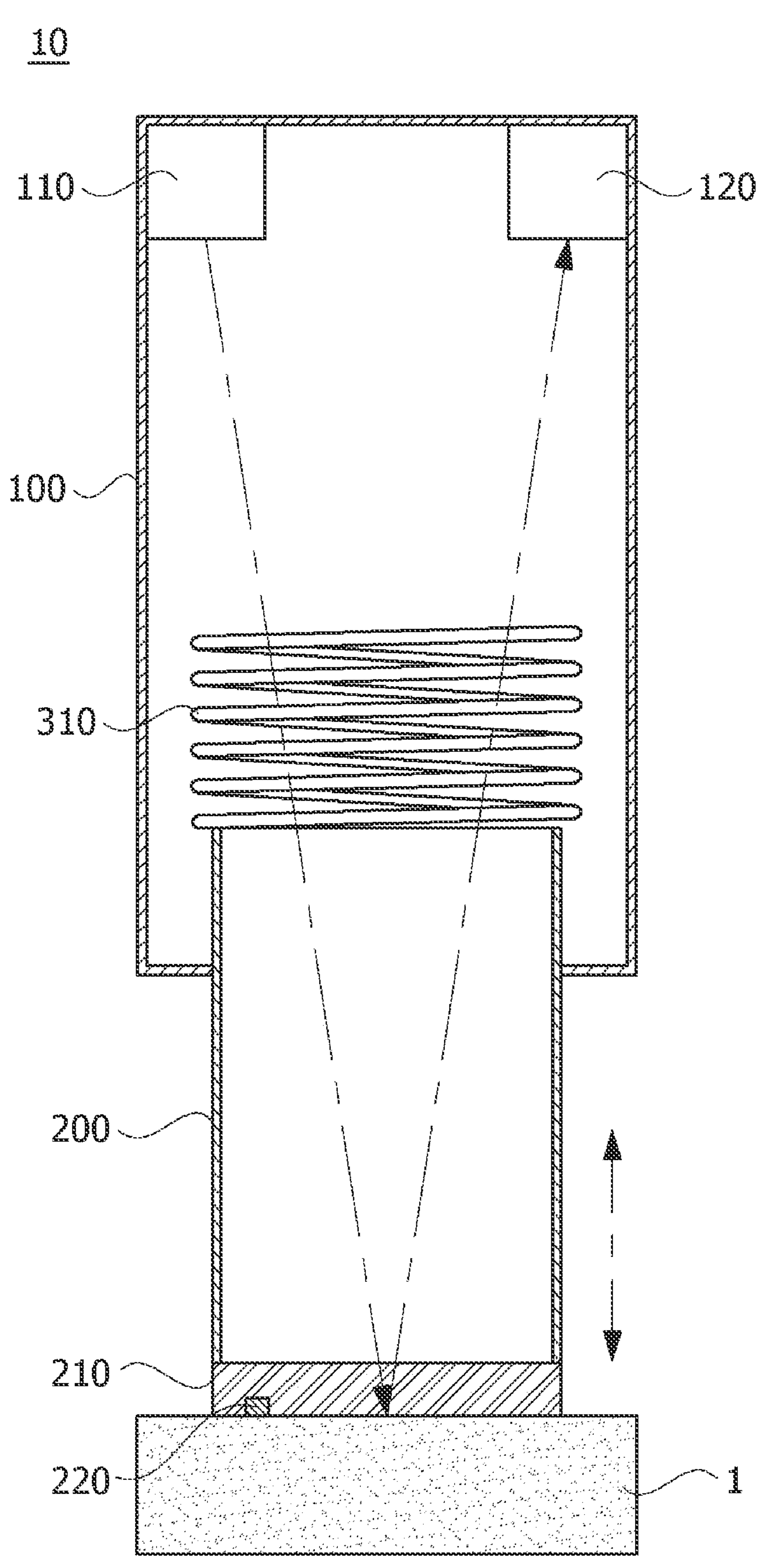

[FIG. 2]
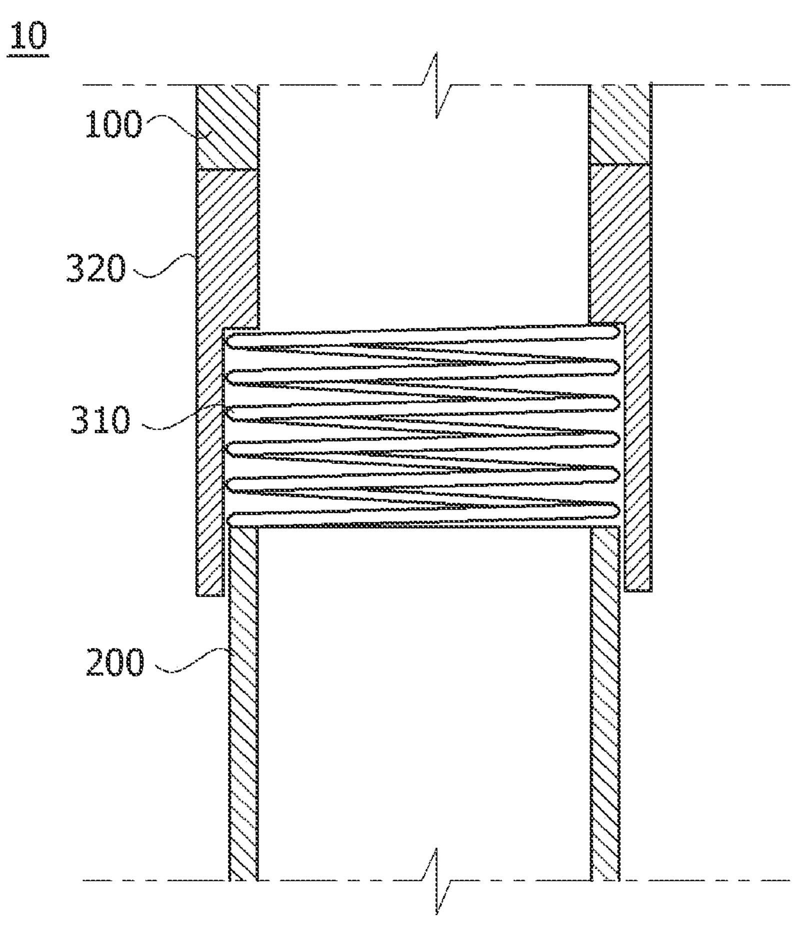

[FIG. 3]
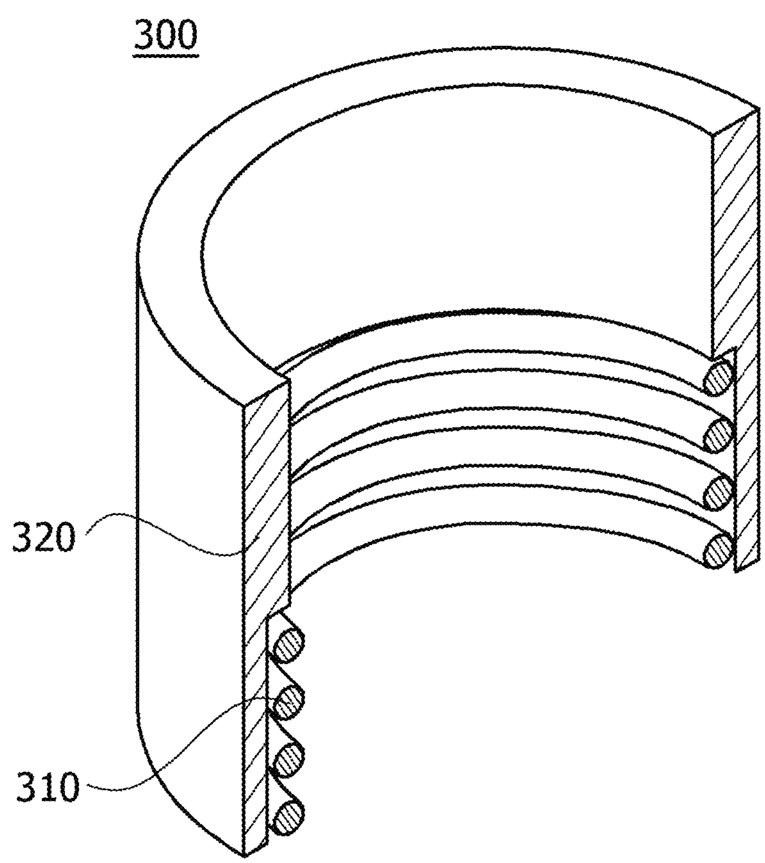

[FIG. 4]
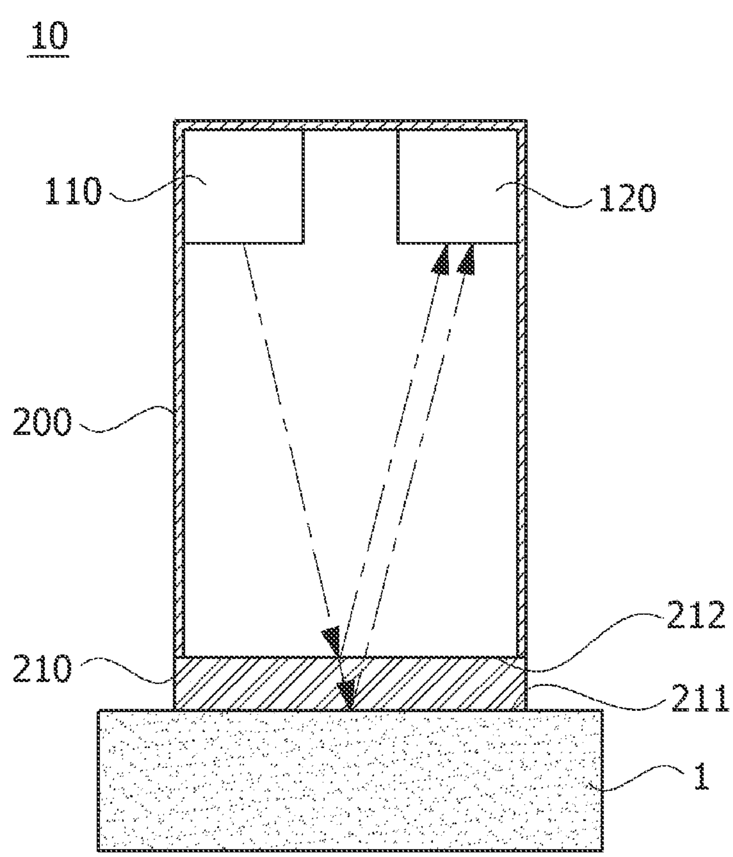

[FIG. 5]
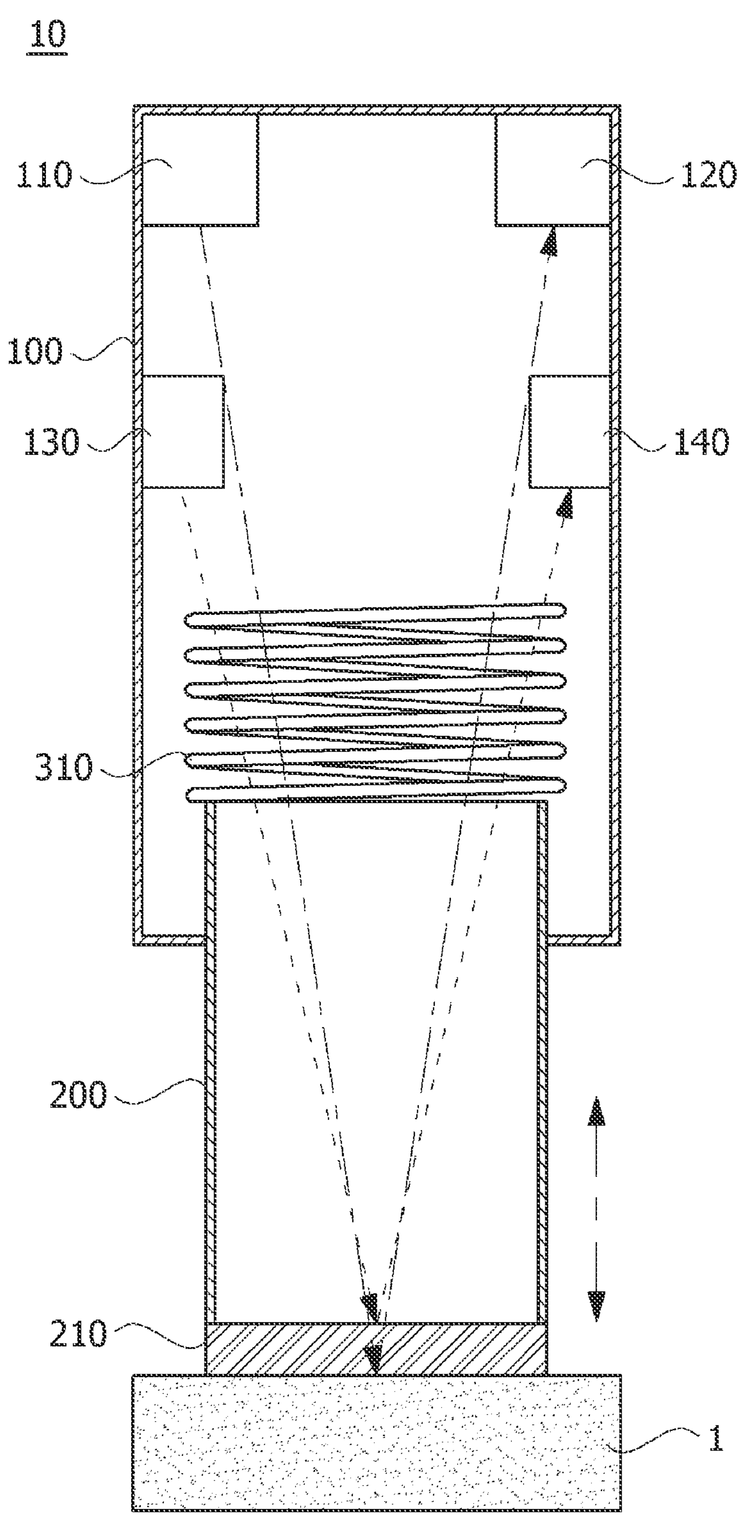

[FIG. 6]
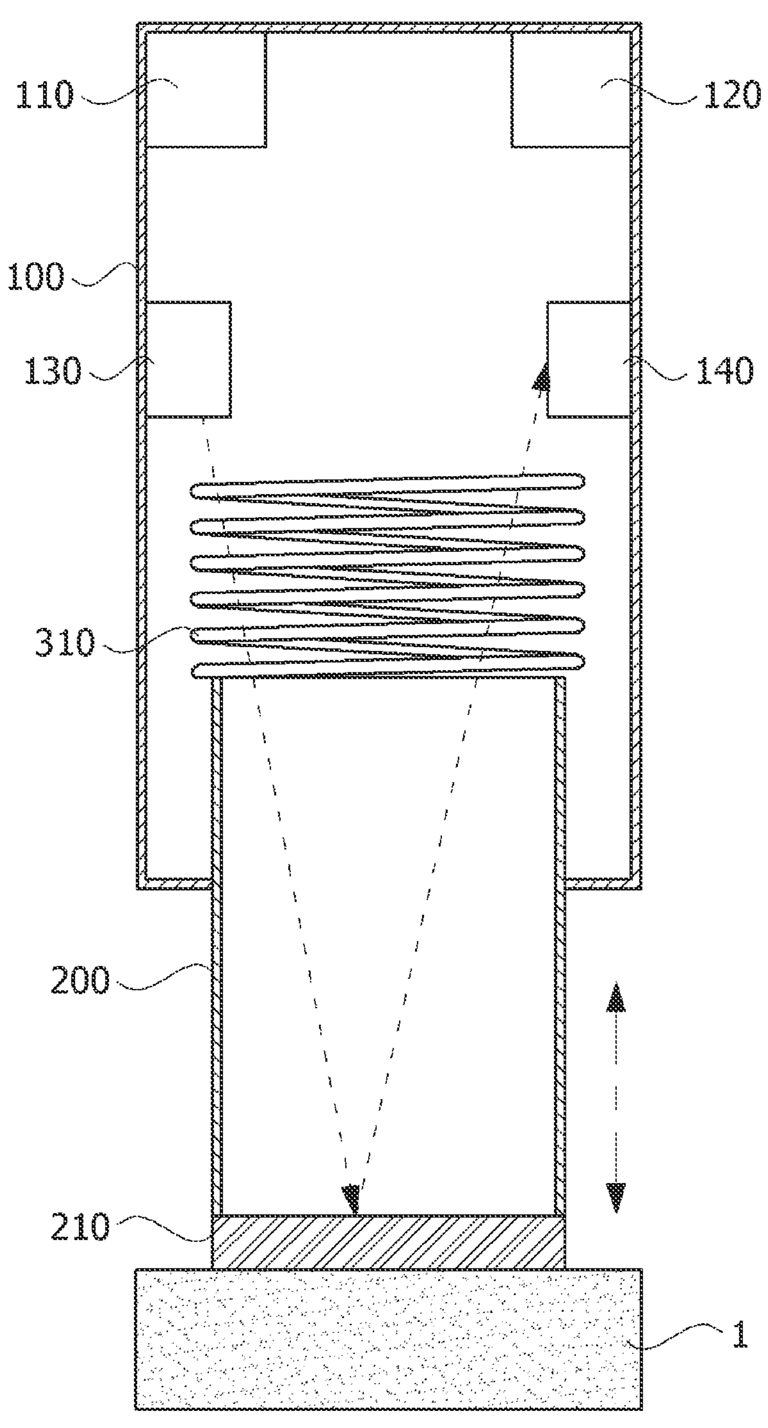

DEVICE AND METHOD FOR PRECISELY MEASURING SKIN MOISTURE

CROSS REFERENCE TO RELATED APPLICATIONS

This application is the U.S. National Stage entry of International Application No. PCT/KR2023/000550, filed on Jan. 12, 2023, which, in turn, claims priority to KR Patent Application No. 10-2022-0164351, filed on Nov. 30, 2022, and KR Patent Application No. 10-2023-0004540, filed on Jan. 12, 2023, the disclosures all of which are hereby incorporated herein by reference in their entireties for all purposes.

TECHNICAL FIELD

The present disclosure relates to a device and method for precisely measuring skin moisture, and more particularly, to a device and method for precisely measuring skin moisture in which measurement of skin moisture is not affected by pressure applied to the device.

BACKGROUND ART

Terahertz (THz) electromagnetic waves are defined as electromagnetic waves having frequencies ranging from 0.1 to 10 THz and wavelengths ranging from 30 μm to 3 mm and simultaneously possess a property of microwaves that are sensitive to moisture and a property of infrared rays that can be used in imaging with a resolution of several hundreds of micrometers.

Imaging technology using THz waves is useful in distinguishing a boundary of skin cancer using the fact that the amount of water contained in normal tissue and the amount of water contained in cancer tissue are different. Also, the imaging technology using THz waves enables spectroscopic analysis for moisture density in skin tissue, thus enabling qualitative analysis for pressure applied to skin tissue.

However, the conventional imaging technology using THz waves has a problem in that measured values are not accurate because reflectance changes due to pressure applied to skin tissue.

DISCLOSURE

Technical Problem

The present disclosure is directed to providing a device and method for precisely measuring skin moisture in which measurement of skin moisture is not affected by pressure applied to the device.

Technical Solution

One embodiment of the present disclosure provides a device for precisely measuring skin moisture, the device including a main body which is open toward a measurement target and has a hollow portion, a light source part configured to irradiate the measurement target with terahertz (THz) waves through the hollow portion, a THz wave detector configured to detect the THz waves reflected from the measurement target, and a contact part slidably mounted on the main body and having a window provided thereon to come in contact with the measurement target, wherein the main body includes a connector which includes an elastic member provided to connect the main body and the contact part and be compressed during sliding of the contact part into the main body.

Also, another embodiment of the present disclosure provides a device for precisely measuring skin moisture, the device including a contact part which is open toward a measurement target and has a hollow portion, a light source part configured to irradiate the measurement target with terahertz (THz) waves through the hollow portion, and a THz wave detector configured to detect the THz waves reflected from the measurement target, wherein the contact part includes a window provided to come in contact with the measurement target, the window has a first surface configured to come in contact with the measurement target and a second surface attached to the contact part and formed in a direction opposite to the first surface, and the THz wave detector separately detects THz waves reflected from the first surface of the window and THz waves reflected from the second surface of the window.

Also, still another embodiment of the present disclosure provides a device for precisely measuring skin moisture, the device including a main body which is open toward a measurement target and has a hollow portion, a light source part configured to irradiate the measurement target with terahertz (THz) waves through the hollow portion, a THz wave detector configured to detect the THz waves reflected from the measurement target, and a contact part slidably mounted on the main body and having a window provided thereon to come in contact with the measurement target, wherein the main body includes a connector configured to connect the main body and the contact part, a laser irradiator configured to irradiate laser toward the window, and a laser detector configured to detect the laser reflected from the window, and the contact part is connected to the main body to be slidable in each of a direction in which the contact part is inserted into the main body and a direction in which the contact part protrudes to an outside of the main body.

Also, one embodiment of the present disclosure provides a method for precisely measuring skin moisture, the method including bringing a window of a contact part in close contact with skin, irradiating terahertz (THz) waves toward the skin, and detecting the THz waves reflected from the skin, wherein, in the bringing of the window in close contact with the skin, an elastic member adjusts pressure applied to the skin.

Also, another embodiment of the present disclosure provides a method for precisely measuring skin moisture, the method including bringing a window of a contact part in close contact with skin, irradiating terahertz (THz) waves toward the skin, and detecting the THz waves reflected from the skin, wherein the detecting of the THz waves includes comparing THz waves reflected from a first surface of the window and THz waves reflected from a second surface of the window.

Also, still another embodiment of the present disclosure provides a method for precisely measuring skin moisture, the method including bringing a window of a contact part in close contact with skin, irradiating laser toward the window, detecting the laser reflected from the window, irradiating terahertz (THz) waves toward the skin, and detecting the THz waves reflected from the skin, wherein, in the detecting of the THz waves, a THz wave detector detects the THz waves when the laser is detected by a laser detector.

Advantageous Effects

According to one embodiment of the present disclosure, when skin moisture is measured using terahertz (THz)

waves, a THz reflection signal can be measured by constantly adjusting pressure applied to the skin.

Also, according to another embodiment of the present disclosure, when skin moisture is measured using THz waves, a THz reflection signal can be measured without being affected by pressure applied to the skin.

In addition, according to still another embodiment of the present disclosure, when skin moisture is measured using THz waves, a THz reflection signal can be measured when pressure applied to the skin is in a predetermined range.

DESCRIPTION OF DRAWINGS

FIG. 1 is a cross-sectional view schematically illustrating a device for precisely measuring skin moisture according to one embodiment of the present disclosure.

FIG. 2 is a cross-sectional view illustrating a connection relation of the device for precisely measuring skin moisture according to one embodiment of the present disclosure.

FIG. 3 is a perspective view illustrating a cross-section of a connector according to one embodiment of the present disclosure.

FIG. 4 is a cross-sectional view schematically illustrating a device for precisely measuring skin moisture according to another embodiment of the present disclosure.

FIG. 5 is a cross-sectional view schematically illustrating a device for precisely measuring skin moisture according to still another embodiment of the present disclosure.

FIG. 6 is a cross-sectional view schematically illustrating an operational state of the device for precisely measuring skin moisture according to still another embodiment of the present disclosure.

MODES OF THE INVENTION

Hereinafter, exemplary embodiments of the present disclosure will be described in more detail with reference to the accompanying drawings.

Also, the same or corresponding components will be denoted by the same or similar reference numerals even when shown in different drawings, and repeated description thereof will be omitted. For convenience of description, the size and shape of each component illustrated in the drawings may be exaggerated or reduced.

FIG. 1 is a cross-sectional view schematically illustrating a device for precisely measuring skin moisture according to one embodiment of the present disclosure, FIG. 2 is a cross-sectional view illustrating a connection relation of the device for precisely measuring skin moisture according to one embodiment of the present disclosure, and FIG. 3 is a perspective view illustrating a cross-section of a connector according to one embodiment of the present disclosure.

Referring to FIGS. 1 to 3, a precise skin moisture measurement device 10 according to one embodiment of the present disclosure may include a main body 100, a light source part 110, a terahertz (THz) wave detector 120, a contact part 200, and a connector 300.

The main body 100 according to one embodiment of the present disclosure may have a tubular form that is open toward a measurement target and has a hollow portion. The measurement target may be skin 1.

The light source part 110 may irradiate the measurement target with THz waves through the hollow portion.

The THz wave detector 120 may detect the THz waves reflected from the measurement target.

Here, the light source part 110 and the THz wave detector 120 may be disposed in the hollow portion of the main body 100 and may be disposed at an upper end of the hollow portion.

Also, the light source part 110 and the THz wave detector 120 may be disposed outside the main body 100 instead of being disposed at the upper end of the hollow portion of the main body 100. Here, the main body 100 may have a form that is open toward the light source part 110 and the THz wave detector 120 to allow THz waves to pass therethrough.

The light source part 110 may further include a light source lens configured to condense the THz waves on the measurement target.

Also, the THz wave detector 120 may further include a light receiving lens configured to condense the THz waves reflected from the measurement target on the THz wave detector 120.

The contact part 200 according to one embodiment of the present disclosure may be slidably mounted on the main body 100 and may have a window 210 provided thereon to come in contact with the measurement target.

Here, the contact part 200 may be connected to the main body 100 to be slidable in each of a direction in which the contact part 200 is inserted into the main body 100 and a direction in which the contact part 200 protrudes to the outside of the main body Also, the contact part 200 may have a tubular form that is open toward the measurement target and the main body 100 and has a hollow portion.

The contact part 200 may include a pressure sensor 220 configured to measure pressure applied to the measurement target. Here, the pressure sensor 220 may be provided at a lower end of the window 210 which is configured to come in contact with the measurement target.

The connector 300 according to one embodiment of the present disclosure may include an elastic member 310 provided to connect the main body 100 and the contact part 200 and be compressed during sliding of the contact part 200 into the main body 100.

The connector 300 may include an elastic member support 320 connected to a lower end of the main body 100 and configured to support the elastic member 310. Here, the main body 100 and the connector 300 may be provided as separate members or integrally provided.

Also, the elastic member 310 of the connector 300 may be connected to an upper end of the contact part 200. Here, the elastic member 310 may be provided in a form that surrounds an outer sidewall of the contact part 200.

Meanwhile, the elastic member 310 may be a spring, but the present disclosure is not limited thereto.

A method for precisely measuring skin moisture according to one embodiment of the present disclosure may include bringing the window 210 of the contact part 200 in close contact with the skin 1, irradiating THz waves toward the skin 1, and detecting the THz waves reflected from the skin 1.

In the bringing of the window 210 in close contact with the skin 1, the user may apply pressure to the precise skin moisture measurement device 10.

The contact part 200 may slide into the main body 100 due to the pressure applied by the user.

Here, the elastic member 310 connected to the contact part 200 may be compressed between the contact part 200 and the elastic member support 320 and adjust pressure applied to the skin 1.

FIG. 4 is a cross-sectional view schematically illustrating a device for precisely measuring skin moisture according to another embodiment of the present disclosure.

Referring to FIG. 4, a precise skin moisture measurement device 10 according to another embodiment of the present disclosure may include a contact part 200, a light source part 110, and a THz wave detector 120.

The contact part 200 according to another embodiment of the present disclosure may have a tubular form that is open toward a measurement target and has a hollow portion. Here, the measurement target may be skin 1.

The light source part 110 may irradiate the measurement target with THz waves through the hollow portion.

The THz wave detector 120 may detect the THz waves reflected from the measurement target.

Here, the light source part 110 and the THz wave detector 120 may be disposed in the hollow portion of the contact part 200 and may be disposed at an upper end of the hollow portion.

Also, the light source part 110 and the THz wave detector 120 may be disposed outside the contact part 200 instead of being disposed at the upper end of the hollow portion of the contact part 200. Here, the contact part 200 may have a form that is open toward the light source part 110 and the THz wave detector 120 to allow THz waves to pass therethrough.

The light source part 110 may further include a light source lens configured to condense the THz waves on the measurement target.

Also, the THz wave detector 120 may further include a light receiving lens configured to condense the THz waves reflected from the measurement target on the THz wave detector 120.

Meanwhile, the contact part 200 may include a window 210 provided to come in contact with the measurement target.

The window 210 may have a first surface 211 configured to come in contact with the measurement target and a second surface 212 attached to the contact part 200 and formed in a direction opposite to the first surface 211.

Here, the THz wave detector 120 may separately detect THz waves reflected from the first surface 211 of the window 210 and THz waves reflected from the second surface 212 of the window 210.

A method for precisely measuring skin moisture according to another embodiment of the present disclosure may include bringing the window 210 of the contact part 200 in close contact with the skin 1, irradiating THz waves toward the skin 1, and detecting the THz waves reflected from the skin 1.

In the irradiating of the THz waves toward the skin 1, the THz waves may be irradiated toward the window 210. Here, some of the THz waves may be reflected from the first surface 211 of the window 210 that has come in contact with the skin 1, and some of the THz waves may be reflected from the second surface 212 of the window 210.

The detecting of the THz waves may include comparing the THz waves reflected from the first surface 211 of the window 210 and the THz waves reflected from the second surface 212 of the window 210.

Specifically, the THz waves reflected from the first surface 211 are reflected from the measurement target and the surface of the window 210 and thus have a THz wave optical constant value that changes according to the measurement target.

Also, the THz waves reflected from the second surface 212 are reflected from air and the surface of the window 210 and thus have a THz wave optical constant value that is always a constant value.

Here, when the optical constant value of the THz waves reflected from the first surface 211 is compared with the optical constant value of the THz waves reflected from the second surface 212, an absolute THz wave optical constant value of the measurement target may be derived.

Therefore, by comparing the THz waves reflected from the first surface 211 and the THz waves reflected from the second surface 212, the user may derive a THz wave optical constant of the skin 1 regardless of the pressure applied to the skin 1. Here, the derived optical constant may include one or more of reflectance, a complex refractive index, complex permittivity, and complex conductivity of the measurement target.

FIG. 5 is a cross-sectional view schematically illustrating a device for precisely measuring skin moisture according to still another embodiment of the present disclosure, and FIG. 6 is a cross-sectional view schematically illustrating an operational state of the device for precisely measuring skin moisture according to still another embodiment of the present disclosure.

Referring to FIGS. 5 and 6, a precise skin moisture measurement device 10 according to still another embodiment of the present disclosure may include a main body 100, a light source part 110, a THz wave detector 120, a contact part 200, and a connector 300.

The main body 100 according to still another embodiment of the present disclosure may have a tubular form that is open toward a measurement target and has a hollow portion. Here, the measurement target may be skin 1.

The light source part 110 may irradiate the measurement target with THz waves through the hollow portion.

The THz wave detector 120 may detect the THz waves reflected from the measurement target.

Here, the light source part 110 and the THz wave detector 120 may be disposed in the hollow portion of the main body 100 and may be disposed at an upper end of the hollow portion.

Also, the light source part 110 and the THz wave detector 120 may be disposed outside the main body 100 instead of being disposed at the upper end of the hollow portion of the main body 100. Here, the main body 100 may have a form that is open toward the light source part 110 and the THz wave detector 120 to allow THz waves to pass therethrough.

The light source part 110 may further include a light source lens configured to condense the THz waves on the measurement target.

Also, the THz wave detector 120 may further include a light receiving lens configured to condense the THz waves reflected from the measurement target on the THz wave detector 120.

The contact part 200 according to still another embodiment of the present disclosure may be slidably mounted on the main body 100 and may have a window 210 provided thereon to come in contact with the measurement target.

Here, the contact part 200 may be connected to the main body 100 to be slidable in each of a direction in which the contact part 200 is inserted into the main body 100 and a direction in which the contact part 200 protrudes to the outside of the main body 100.

Also, the contact part 200 may have a tubular form that is open toward the measurement target and the main body 100 and has a hollow portion.

Meanwhile, the main body 100 may include a laser irradiator 130 configured to irradiate laser toward the window 210 and a laser detector 140 configured to detect the laser reflected from the window 210.

Here, the laser irradiator 130 may be disposed at one side surface of the hollow portion of the main body 100, and the laser detector 140 may be disposed at the other side surface of the hollow portion of the main body 100.

The connector 300 according to still another embodiment of the present disclosure may connect the main body 100 and the contact part 200.

The connector 300 may include an elastic member 310 connected to an upper end of the contact part 200 and an elastic member support 320 connected to a lower end of the main body 100 and configured to support the elastic member 310.

Here, the elastic member 310 may be provided to be compressed during sliding of the contact part 200 into the main body 100.

Also, the elastic member 310 may be provided in a form that surrounds an outer sidewall of the contact part 200.

Here, the main body 100 and the connector 300 may be provided as separate members or integrally provided.

Meanwhile, the elastic member 310 may be a spring, but the present disclosure is not limited thereto.

A method for precisely measuring skin moisture according to still another embodiment of the present disclosure may include bringing the window 210 of the contact part 200 in close contact with the skin 1, irradiating laser toward the window 210, detecting the laser reflected from the window 210, irradiating THz waves toward the skin 1, and detecting the THz waves reflected from the skin 1.

In the bringing of the window 210 in close contact with the skin 1, the user may apply pressure to the precise skin moisture measurement device 10.

The contact part 200 may slide into the main body 100 due to the pressure applied by the user.

Here, the elastic member 310 connected to the contact part 200 may be compressed between the contact part 200 and the elastic member support 320. Thus, a distance between the laser irradiator 130 and the window 210 may be changed according to the pressure applied by the user.

In the detecting of the laser, a position that the laser reflected from the window reaches may be determined according to the distance between the laser irradiator 130 and the window 210, and the laser detector 140 may detect the laser that has reached a specific position.

In the irradiating of the THz waves, the light source part 110 may continuously irradiate the THz waves or may irradiate the THz waves only when the laser is detected by the laser detector 140.

In the detecting of the THz waves, the THz wave detector 120 may detect the THz waves when the laser is detected by the laser detector 140. Thus, the user may detect the THz waves when a specific pressure is applied to the precise skin moisture measurement device 10.

The exemplary embodiments of the present disclosure described above are disclosed for illustrative purposes. Those of ordinary skill in the art to which the present disclosure pertains may make various modifications and changes within the technical spirit of the present disclosure, and such modifications and changes belong to the protection scope of the present disclosure.

INDUSTRIAL APPLICABILITY

According to a device and method for precisely measuring skin moisture that relate to one embodiment of the present disclosure, during measurement of skin moisture, skin cancer in skin tissue can be precisely diagnosed without being affected by pressure applied by a user.

The invention claimed is:

1. A device for precisely measuring skin moisture, the device comprising:

a main body which is open toward a measurement target and has a hollow portion;

a light source part configured to irradiate the measurement target with terahertz (THz) waves through the hollow portion;

a THz wave detector configured to detect the THz waves reflected from the measurement target; and a contact part slidably mounted on the main body and having a window provided thereon to come in contact with the measurement target, wherein the main body includes a connector configured to connect the main body and the contact part, a laser irradiator configured to irradiate laser toward the window, and a laser detector configured to detect the laser reflected from the window, the contact part is connected to the main body to be slidable in each of a direction in which the contact part is inserted into the main body and a direction in which the contact part protrudes to an outside of the main body, and wherein the THz wave detector detects the THz waves when the laser is detected by the laser detector.

2. The device of claim 1, wherein the laser irradiator is disposed at one side surface of the hollow portion, and the laser detector is disposed at the other side surface of the hollow portion.

3. The device of claim 1, wherein the light source part and the THz wave detector are disposed in the hollow portion of the main body.

4. The device of claim 1, wherein:

the light source part further includes a light source lens; and the THz wave detector further includes a light receiving lens.

5. The device of claim 1, wherein the connector includes:

an elastic member connected to an upper end of the contact part; and an elastic member support connected to a lower end of the main body and configured to support the elastic member, and the elastic member is provided to be compressed during sliding of the contact part into the main body.

6. A method for precisely measuring skin moisture using the device of claim 1, the method comprising:

bringing the window of the contact part in close contact with the skin;

irradiating the laser toward the window, detecting the laser reflected from the window, irradiating the THz waves toward the skin; and detecting the THz waves reflected from the skin, wherein, in the detecting of the THz waves, the THz wave detector detects the THz waves when the laser is detected by the laser detector.

* * * * *